(12) United States Patent
Bathelet et al.

(10) Patent No.: US 7,098,440 B2
(45) Date of Patent: Aug. 29, 2006

(54) METHOD AND APPARATUS FOR INSPECTING HOT HOLLOW ARTICLES THAT ARE TRANSLUCENT OR TRANSPARENT

(75) Inventors: Guillaume Bathelet, Marcy L'etoile (FR); Marc Gerard, Saint Just Sauvage (FR)

(73) Assignee: Tiama, Montagny (FR)

( * ) Notice: Subject to any disclaimer, the term of this patent is extended or adjusted under 35 U.S.C. 154(b) by 113 days.

(21) Appl. No.: 10/834,120

(22) Filed: Apr. 29, 2004

(65) Prior Publication Data

US 2004/0262523 A1 Dec. 30, 2004

(30) Foreign Application Priority Data

Apr. 30, 2003 (FR) .................................. 03 05320

(51) Int. Cl.
*G06M 7/00* (2006.01)
(52) U.S. Cl. ................... 250/221; 250/223 B
(58) Field of Classification Search ............ 250/223 B, 250/559.4, 221, 338.1, 223 R; 356/239.1, 356/239.4, 239.2
See application file for complete search history.

(56) References Cited

U.S. PATENT DOCUMENTS 3,356,212 A 12/1967 Landin
5,583,337 A * 12/1996 Chan .......................... 250/330
6,089,108 A 7/2000 Lucas
6,151,064 A 11/2000 Connolly et al.

FOREIGN PATENT DOCUMENTS

| DE | 19838858 | 4/1999 |
|---|---|---|
| DE | 19902316 | 8/2000 |
| DE | 10030649 | 1/2002 |
| EP | 0679883 | 4/1995 |
| JP | 11136440 | 5/1999 |

* cited by examiner

*Primary Examiner*—Georgia Epps
*Assistant Examiner*—Tony Lu
(74) *Attorney, Agent, or Firm*—Clark & Brody

(57) ABSTRACT

The invention provides a method of using at least one sensor sensitive to infrared radiation for inspecting hollow, transparent or translucent articles at high temperature leaving various different forming cavities. The method includes a step of evaluating the level of infrared radiation from the articles coming from the forming cavities so as to adapt the exposure of the sensor in a subsequent step of inspecting the articles in such a manner as to cause the response of the sensor to be uniform regardless of the different cavities from which the articles come.

17 Claims, 2 Drawing Sheets

METHOD AND APPARATUS FOR INSPECTING HOT HOLLOW ARTICLES THAT ARE TRANSLUCENT OR TRANSPARENT

The present invention relates to the technical field of inspecting hollow articles or objects that are translucent or transparent and that present a high temperature.

More precisely, the invention seeks to inspect glass flasks or bottles leaving a fabrication or forming machine at a high rate.

BACKGROUND OF THE INVENTION

In the preferred field of fabricating glass articles, it is known to use the infrared radiation emitted by the articles leaving the machine for inspection or quality control purposes in order to detect any defects on the surface or inside the articles. It is necessary to perform quality control on such articles in order to eliminate those articles that present defects that might spoil their appearance, or worse, that might constitute a real danger for a subsequent user.

In conventional manner, the forming machine is constituted by a plurality of cavities, each fitted with a mold in which the article takes its final shape at high temperature. At the outlet from the forming machine, the articles are conveyed so as to constitute a line on a transport conveyor causing the articles to travel successively through various treatment stations such as spraying and annealing stations.

It would be advantageous to identify any forming defect as early as possible on leaving the forming machine and prior to treatment in the various treatment stations so as to be able to correct the defect in the forming machine as soon as possible. In the state of the art, various solutions have been proposed for inspecting high temperature articles leaving a forming machine.

For example, patent EP 0 679 883 describes apparatus constituted by two infrared sensors disposed on either side of a conveyor conveying articles at the outlet from the forming machine. Each of those sensors generates a signal in response to the heat radiation emitted by the articles. If such a signal does not correspond to a predetermined model, the articles are considered as being defective. It should be observed that that detection technique consists, for each cavity, in storing the image of an article that is deemed to be good in order to act as a reference model.

Such apparatus does not give satisfaction in practice for reasons which are set out in particular in document DE 199 02 316. It should be observed that the distances articles travel between the various cavities and the sensor used for inspection purposes are very different. However the articles cool very quickly, such that the infrared radiation from each article differs greatly on going past the sensor. In document DE 199 02 316, it is specified that the infrared radiation from the articles going past the sensor can vary in a ratio of 1 to 10, with the ratio being a function of the cavity from which each article originates.

In an attempt to provide a solution to that problem, document DE 199 02 316 proposes analyzing the thermal profile of the articles as picked up by the infrared sensor in order to determine statistically for each cavity an estimated thermal profile which is compared with the measured thermal profile in order to detect whether an article is or is not faulty.

The technique described by that document requires a plurality of thermal profiles to be analyzed statistically and inevitably leads to an approximation that affects the quality of detection. In addition, such a method does not enable a direct comparison to be performed between articles coming from different cavities. Finally, that technique makes use of measurement signals that can become saturated, thereby harming the quality of detection.

In the state of the art, it is also known to adjust a sensor so that the measurement signal is never saturated regardless of the cavity from which an article originates. Nevertheless, insofar as the level of infrared radiation varies over a large range as a function of the originating cavity, the level of the signal delivered by the sensor differs very greatly from one cavity to another. Thus, the level of the measurement signal is very weak for articles coming from the cavities that are furthest from the measurement sensor. Under such circumstances, the signal-to-noise ratio is poor, thereby restricting the ability to detect defects and also harming the quality with which defects are detected. Furthermore, that technique, like other known techniques, involves the use, after the measurement has been acquired, of correction means (such as a reference model (EP 0 679 883) or statistical analysis (DE 199 02 316)) presenting a degree of approximation that is harmful to quality of detection.

OBJECTS AND SUMMARY OF THE INVENTION

The object of the invention is thus to remedy the drawbacks set out above by proposing a method enabling the response of the sensor to be optimized regardless of the forming cavities from which the articles come.

In order to achieve such an object, the method of using at least one infrared radiation sensor to inspect hollow, transparent or translucent articles at high temperature coming from different forming cavities includes a step of evaluating the level of the infrared radiation from the articles coming from the forming cavities in such a manner as to adapt the exposure of the sensor during a subsequent step of inspecting the articles, in order to make the response of the sensor uniform regardless of the different cavities from which the articles come.

The invention thus seeks to act directly on the sensor in order to optimize its response so as to obtain the best signal-to-noise ratio regardless of the cavity from which the article passing the sensor originates. It follows that it is not necessary to use means for correcting the response of the sensor as a function of originating cavity. Furthermore, the signals delivered by the sensor present levels that are identical, thus enabling comparisons to be made directly.

Preferably, the method consists in adapting the exposure of the sensor in such a manner that the sensor for inspecting the articles delivers output signals presenting a maximum amplitude that is not saturated.

In a variant implementation, the method consists in evaluating the level of the infrared radiation by means of a detector other than the sensor.

In another preferred implementation, the method of the invention consists:

in evaluating the infrared radiation level by means of the sensor during a calibration stage during which said evaluation is synchronized with the originating cavities in which the articles are formed; and in adapting the exposure of the sensor for the purpose of inspecting the articles by that sensor as a function of the infrared radiation level as previously evaluated during the calibration stage, this correction being synchronized with the originating cavities in which the articles are formed.

According to an advantage of this preferred variant implementation, during the calibration stage, the infrared radiation level of the articles is evaluated for articles that act as references corresponding to at least a first cycle of forming articles coming from the forming cavities.

According to another advantage of this preferred variant implementation, the method consists in evaluating the level of infrared radiation during a calibration stage that is performed during the step of inspecting a series of articles.

Advantageously, the method consists in adapting the exposure of the sensor by adjusting its integration time.

In other variant implementations, the method consists in adapting the exposure of the sensor by adjusting the exposure time of the sensor, the level of radiation acquired by the sensor, or the gain of signals delivered by the sensor.

Another object of the invention is to provide an installation for inspecting hollow transparent or translucent articles at high temperature coming from different forming cavities. The installation comprises:

at least one sensor sensitive to the infrared radiation emitted by the articles traveling past the sensor; and a control and processor unit for processing the output signals delivered by the sensor.

According to the invention, the installation comprises:

means for evaluating the infrared radiation level, at least in part, of articles prior to inspecting the articles by means of the sensor; and means for adapting the exposure of the sensor as a function of the evaluated infrared radiation level in order to make the response of the sensor uniform during article inspection, regardless of the various different cavities from which the articles come.

In a variant embodiment, the installation includes an infrared radiation detector situated upstream from the sensor in the article travel direction and connected to the control and processor unit.

In a preferred variant embodiment, the means for evaluating the level of infrared radiation from the articles are implemented by using the sensor(s).

Advantageously, the means for adjusting sensor exposure ensure that the sensor delivers output signals presenting a maximum amplitude that is not saturated.

In a preferred variant embodiment, the installation includes as means for adapting the exposure of the sensor, means for adjusting the integration time of the sensor.

In a preferred embodiment, the installation includes synchronization means between the control unit of the sensor and the forming machine in order to synchronize the correction of the exposure of the sensor past which the articles travel as a function of the originating cavities in which said articles are formed.

In a preferred variant embodiment, the installation includes at least two sensors sensitive to infrared radiation placed on either side of a conveyor for moving the articles past the sensors, each sensor being inclined relative to the normal to the travel direction at an angle of inclination that is less than or equal to 45°, and that is preferably about 30°.

In a preferred embodiment, the installation includes, for each sensor, a plate that is opaque to infrared radiation and that is disposed in such a manner that the article lies between said plate and the field of view of the sensor so as to avoid the sensor picking up interference illumination.

BRIEF DESCRIPTION OF THE DRAWINGS

Various other characteristics appear from the following description made with reference to the accompanying drawings which show, as non-limiting examples, embodiments of the invention.

MORE DETAILED DESCRIPTION

Figure 1:
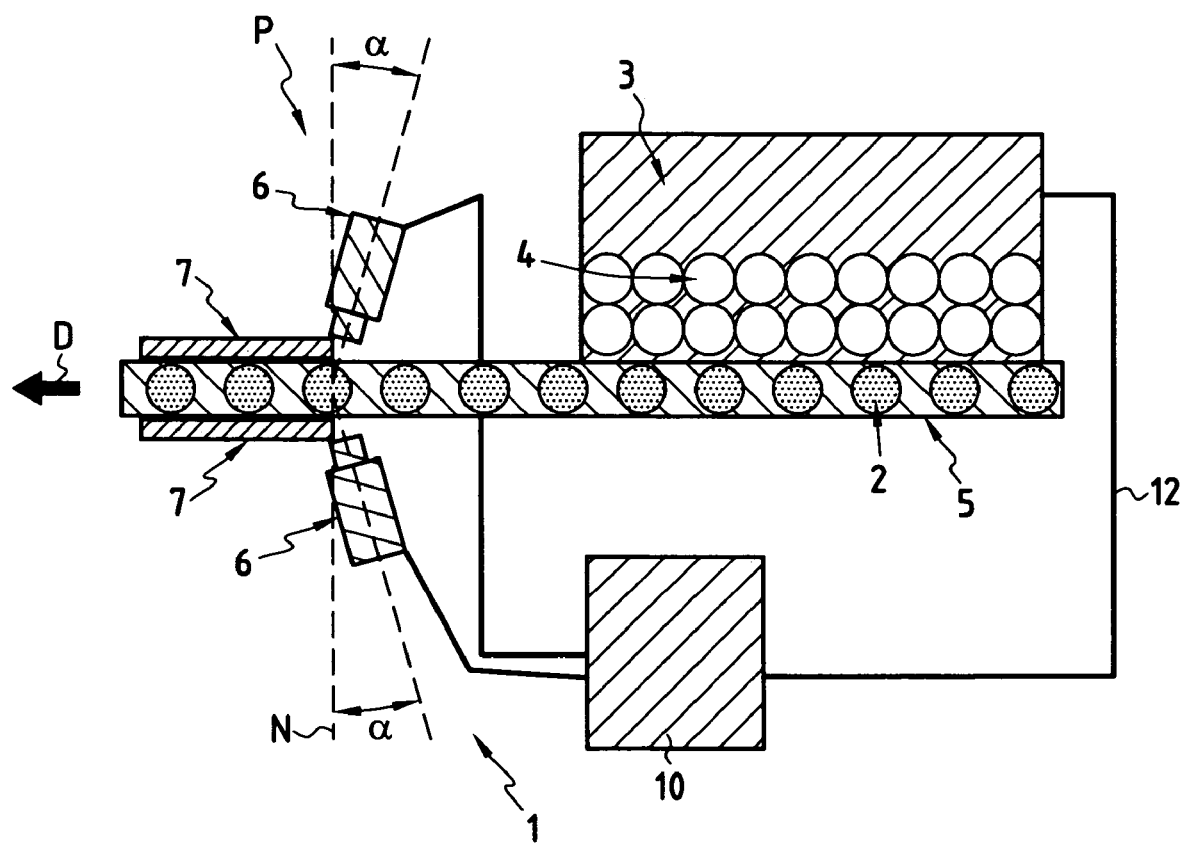
FIG. 1 is a diagrammatic view showing an embodiment of an installation in accordance with the invention.

As can be seen more clearly in FIG. 1, the invention relates to an installation 1 enabling hollow, transparent or translucent articles 2 such as glass flasks or bottles, for example, to be inspected while hot. The installation 1 is placed in such a manner as to enable the articles 2 leaving a fabrication or forming machine 3 and thus presenting high temperature to be inspected.

In conventional manner, the forming machine 3 comprises a series of cavities 4 each serving to form a respective article 2. In conventional manner, the articles 2 that have just been formed by the machine 3 are taken by an output conveyor 5 so that the articles 2 constitute a line on the conveyor 5. The articles 2 are thus taken successively to various treatment stations.

In accordance with the invention, the installation 1 comprises a quality control or inspection station P that operates at a high rate of throughput and that inspects the articles 2 while they present high temperature. To this end, the inspection station P is placed very close to the forming machine so that the conveyor 5 causes successive high-temperature articles 2 to travel past the inspection station P, thus making it possible, in line, to verify whether the articles 2 are or are not defective. The inspection station P comprises at least one, and in the example shown two, sensors 6 that are sensitive to the infrared radiation emitted by the articles 2 traveling past each sensor. The sensors 6 are thus placed at the outlet from the forming machine 3 in such a manner as to be sensitive to the heat radiation emitted by the articles 2. In the example shown, two sensors 6 are placed on either side of the conveyor 5 so as to enable both sides of each article 2 to be inspected. For example, each sensor 6 is constituted by a linear type infrared camera.

In a preferred embodiment, each sensor 6 is inclined relative to the normal and to the travel direction D at an angle of inclination α that is less than or equal to 45°, and that is preferably about 30°. It should be observed that each sensor is pointed so as to observe an article 2 that is downstream therefrom relative to the article travel direction D. The two sensors 6 are thus disposed symmetrically on either side of the conveyor 5.

In another preferred embodiment, for each sensor 6, the installation includes a plate 7 that is opaque to infrared radiation and that is placed in such a manner that the article 2 is situated between said plate 7 and the field of view of the sensor 6. Such an opaque plate 7 makes it possible to avoid the sensor 7 picking up interfering heat radiation.

In conventional manner, the sensors 6 are connected to a control unit 10 for processing the output signals delivered by the sensors 6. Each sensor 6 generates a respective output signal, e.g. a video signal, in response to the infrared radiation emitted by an article 2. Naturally, the unit 10 is adapted to control the operation of the sensors 6 as an article 2 is traveling through their fields of view, in such a manner that each sensor 6 takes an image of each of the articles 2 traveling at a high rate of throughput. The images taken by the sensor(s) 6 are analyzed by the unit 10 during an inspection step in order to look for possible defects in the articles 2.

In accordance with the invention, the installation 1 includes means enabling the level or the intensity of the infrared radiation from the articles 2 to be evaluated at least in part prior to the articles being inspected by the sensor(s) 6. Such evaluation means may be implemented by an infrared radiation detector different from the sensor(s) and placed upstream from the inspection station P in the travel direction of the articles 2. In this example, such a detector is connected to the control and processing unit 10.

In a preferred variant embodiment that is described in greater detail below, such evaluation means are implemented by the sensor(s) 6 during a calibration stage during which the infrared radiation from the articles 2 coming from each of the cavities 4 is recorded. Thus, these means evaluate the amplitude of the output signal in the images acquired by the sensor(s) 6 for articles coming from different cavities 4. For example, this evaluation of infrared radiation level is performed on a predetermined portion of each image that is taken.

It should be observed that the installation 1 includes synchronizing means 12 for synchronizing the control unit 10 with the forming machine 3 so that, for each article 2 going past the detection station P, it can be aware of the cavity from which the article comes. Thus, partial or complete measurement of the infrared radiation from the articles 2 is synchronized with the forming machine 3. In other words, for each cavity 4, the level of infrared radiation from the article 2 delivered by said cavity 4 is evaluated.

In accordance with the invention, the installation also includes means for adapting the exposure of the sensor(s) 6 as a function of the previously evaluated infrared radiation level so as to cause the response of the sensor(s) during inspection of the articles to be made uniform regardless of the different cavities from which the articles come. It should be considered that the distances traveled between the various cavities 4 and the inspection station P are very different. Since the articles 2 cool very quickly, the infrared radiation levels from the various articles are very different at the time they go past the inspection station P.

Such a phenomenon will be better understood on examining the diagrams of FIGS. 2A, 2B, and 3A, 3B which show examples of the video signals generated by an analog camera 6 as an article 2 goes past. The abscissa axis in each diagram represents time, while the ordinate axis represents the output voltage generated by the sensor 6 as a function of the intensity of the radiation it receives.

Figure 2A:
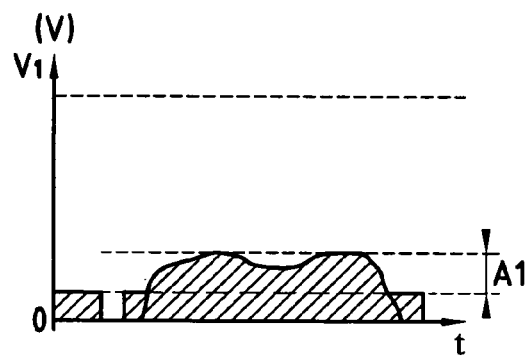
FIGS. 2A and 2B show the form of signals delivered by a sensor implementing the principle of the invention for two cavities that are far apart from each other.

FIG. 2A shows the form of the output signal $V_1$ from a sensor 6 corresponding to the infrared radiation from an article 2 fabricated by the forming cavity 4 that is furthest from the inspection station P.

Figure 2B:
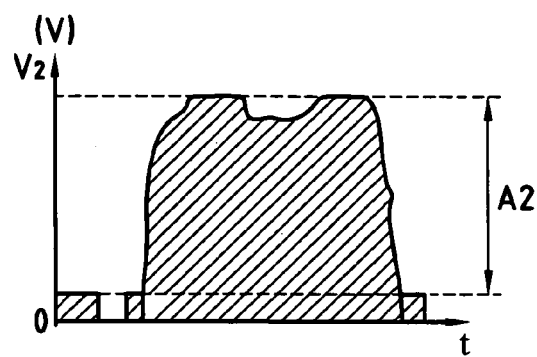
Figure 3A:
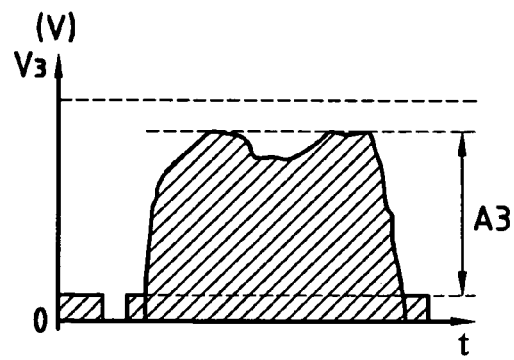
FIGS. 3A and 3B show the form of the signals output by a sensor implementing the principle of the invention, for two cavities that are far apart from each other.
Figure 3B:
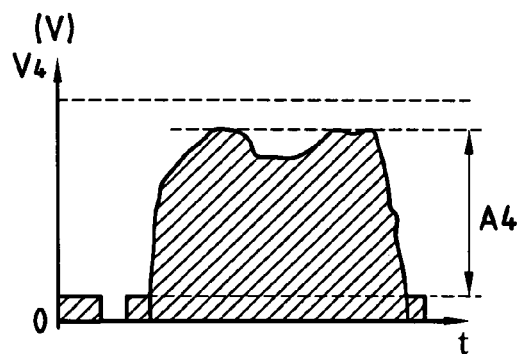

FIG. 2B shows the form of the output signal $V_2$ from a sensor 6 that corresponds to the infrared radiation from an article 2 coming from the cavity 4 that is closest to the detection station P.

The amplitude $A_1$ of the output signal $V_1$ corresponding to the cavity 4 that is furthest away is thus very low compared with the amplitude $A_2$ of the output signal $V_2$ corresponding to an article coming from the cavity which is closest to the detection station P. In the prior art, it thus appeared to be impossible to obtain a good dynamic range and a good signal-to-noise ratio for all of the articles coming from the various cavities 4.

In accordance with the invention, provision is made during article inspection to adapt the exposure of each sensor 6 as a function of the previously evaluated level of the infrared radiation, thereby enabling the response of the sensor to be made uniform. Thus, as can be seen more precisely from FIGS. 3A and 3B, with the correction of the invention, the amplitudes $A_3$ and $A_4$ of the output signals $V_3$ and $V_4$ corresponding to articles coming respectively from the furthest-away cavity and from the nearest cavity are substantially homogeneous or identical. In other words, the exposure of each sensor 6 is corrected during the step of inspecting the article 2 by means of an adjustment that is adapted as a function of the cavity 4 from which the article being inspected has come. The output signals from each of the sensors 6 can thus present amplitude that is homogeneous or constant regardless of the cavity from which an article 2 has come.

Advantageously, the exposure of each sensor 6 is adapted so that each sensor 6 for inspecting articles delivers output signals presenting a maximum amplitude that is not saturated so as to optimize the dynamic range and the signal-to-noise ratio of the signal from the sensor.

Various methods are possible for adapting the exposure of a sensor 6. For example, an automatic iris system can be used for automatically closing the diaphragm of the sensor objective lens once a predetermined light level has been reached.

Another technique consists in adjusting gain differently within the measurement acquisition system as a function of cavity 4. The gain corresponding to a cavity 4 is stored and is applied whenever an article corresponding to that cavity is going past.

Another method is to adjust the exposure time of the sensor by a controlled mechanical or electronic shutter.

Advantageously, it is preferable to use a camera having an integration time that is adjustable in order to adjust the exposure of the camera. Integration time is the time during which the sensitive surface of the camera is exposed to light prior to transferring its electrical charge. This time is a fraction of the line period of the camera. Such a solution presents the advantage of keeping optical adjustments that are identical and of providing the best signal-to-noise ratio regardless of the different levels of infrared radiation from the articles 2.

It should be observed that the invention makes it possible to compensate continuously for variations in the mean temperature of articles due to changes in the forming method or to external elements, without degrading inspection.

The installation 1 of the invention also enables an inspection method to be implemented that stems directly from the above description.

The method described below relates to a posteriori evaluation of the infrared radiation emitted by each article 2. In this technique, the unit 10 is synchronized with the forming machine 3 so as to be continuously aware of the different cavities 4 from which articles 2 have come. The method consists in implementing a calibration stage during which the infrared level coming from articles 2 traveling past the inspection station P is evaluated in full or in part. Such evaluation is synchronized with the forming origins of the articles in the cavities so that for each article 2 going past the inspection station P, the cavity 4 from which the article comes is known.

Thus, during a subsequent step of inspecting the articles by means of the sensor(s), the exposure of each sensor 6 is adapted as a function of the level of infrared radiation as previously evaluated during the calibration stage so as to make sensor response uniform regardless of the different cavities from which articles come. The exposure of each camera 6 is thus corrected with an adjustment that takes account for each article of its forming origin so as to obtain output signals of constant amplitude without saturation for all of the articles. In this way, and as explained above, it is possible to obtain an image without saturation and with an amplitude that is maximum and constant regardless of the cavity from which the article comes. This maximizes dynamic range and provides the best signal-to-noise ratio in the images for analysis.

In the example described, during the calibration stage, the level of infrared radiation from the articles 2 is evaluated for articles that are used as references corresponding to at least a first cycle for forming articles coming from the forming cavities 4. In the example described where the sensor is used both for evaluating radiation level and for inspecting an article, it is clear that for the articles that are used as references, the inspection operation cannot be performed with the same level of performance. Naturally, it might be envisaged that evaluating infrared radiation during a calibration stage corresponds to evaluating radiation during the step of inspecting a series of articles. In this way, it is possible to correct the exposure of each sensor 6 as a function of the cavity 4 from which an article 2 originates not only at the beginning of a cycle for fabricating a batch of articles, but throughout such a cycle, so as to keep track of changes influencing the level of radiation from the articles 2 in the inspection station P.

The unit 10 serves to perform quality control or inspection on an image acquired for each article by the sensor(s) 6 without comparison with a predetermined model, given the uniformity obtained amongst the images. Quality control or inspection consists in direct processing of the images taken, in which a search is made for defects. An article is rejected if a defect is detected in any of various characteristics, for example a surface defect, a shape defect, a contrast defect, or an intensity defect. The levels to which thresholds for processing such defects are set are the same regardless of the cavity from an article originates. Such unique adjustments make operation easier, and ensure excellent reproducibility of the adjustments.

The invention is not limited to the examples described and shown since various modifications can be applied thereto without going beyond its ambit.

What is claimed is:

1. A method of using at least one sensor sensitive to infrared radiation for inspecting hollow, transparent or translucent articles at high temperature coming from different forming cavities, the method including a step of evaluating the level of the infrared radiation from the articles coming from the forming cavities and adapting the exposure of the sensor during a subsequent step of inspecting the articles, in order to make the response of the sensor uniform regardless of the different cavities from which the articles come.

2. A method according to claim 1, wherein the exposure of the sensor is adapted in such a manner that the sensor for inspecting the articles delivers output signals presenting a maximum amplitude that is not saturated.

3. A method according to claim 1, wherein the level of the infrared radiation is evaluated by means of a detector other than the sensor.

4. A method according to claim 1, wherein the infrared radiation level is evaluated by means of the sensor during a calibration stage during which said evaluation is synchronized with the originating cavities in which the articles are formed; and in the step of adapting the exposure of the sensor for the purpose of inspecting the articles by that sensor as a function of the infrared radiation level as previously evaluated during the calibration stage, this correction is synchronized with the originating cavities in which the articles are formed.

5. A method according to claim 4, wherein, during the calibration stage, the infrared radiation level of the articles is evaluated for articles that act as references corresponding to at least a first cycle of forming articles coming from the forming cavities.

6. A method according to claim 4, wherein the level of infrared radiation is evaluated during a calibration stage that is performed during the step of inspecting a series of articles.

7. A method according to claim 1, wherein the exposure of the sensor is adapted by adjusting its integration time.

8. A method according to claim 1, wherein the exposure of the sensor is adapted by adjusting the exposure time of the sensor, the level of radiation acquired by the sensor, or the gain of signals delivered by the sensor.

9. An installation for inspecting hollow, transparent or translucent articles while hot on leaving forming cavities, the installation comprising: at least one sensor sensitive to the infrared radiation emitted by the articles traveling past the sensor; and a control and processor unit for processing the output signals delivered by the sensor, the installation further comprising: means for evaluating the infrared radiation level, at least in part, of articles prior to inspecting the articles by means of the sensor; and means for adapting the exposure of the sensor as a function of the evaluated infrared radiation level in order to make the response of the sensor uniform during article inspection, regardless of the various different cavities from which the articles come.

10. An installation according to claim 9, wherein the means for evaluating the level of infrared radiation from the articles are implemented by using the sensor(s).

11. An installation according to claim 9, including an infrared radiation detector situated upstream from the sensor in the article travel direction and connected to the control and processor unit.

12. An installation according to claim 9, wherein the means for adjusting sensor exposure ensure that the sensor delivers output signals presenting a maximum amplitude that is not saturated.

13. An installation according to claim 9, including as means for adapting the exposure of the sensor, means for adjusting the integration time of the sensor.

14. An installation according to claim 9, including synchronization means between the control unit of the sensor and the forming machine in order to synchronize the correction of the exposure of the sensor past which the articles travel as a function of the originating cavities in which said articles are formed.

15. An installation according to claim 9, including at least two sensors sensitive to infrared radiation placed on either side of a conveyor for moving the articles past the sensors, each sensor being inclined relative to the normal to the travel direction at an angle of inclination that is less than or equal to 45°.

16. An installation according to claim 9, including, for each sensor, a plate that is opaque to infrared radiation and that is disposed in such a manner that the article lies between said plate and the field of view of the sensor so as to avoid the sensor picking up interference illumination.

17. An installation according to claim 15, wherein the angle of inclination is about 30°.

* * * * *